United States Patent [19]

Eberle et al.

[11] Patent Number: 5,135,486
[45] Date of Patent: Aug. 4, 1992

[54] SELF-VENTING BALLOON DILITATION CATHETER

[75] Inventors: Michael J. Eberle; Tim Cortez, both of Citrus Heights, Calif.

[73] Assignee: Endosonics Corporation, Rancho Cordova, Calif.

[21] Appl. No.: 575,976

[22] Filed: Aug. 31, 1990

[51] Int. Cl.⁵ .................................... A61M 29/00
[52] U.S. Cl. ........................... 604/96; 606/194
[58] Field of Search ............ 606/192, 194; 604/95, 604/96, 99; 600/18

[56] References Cited

U.S. PATENT DOCUMENTS

| | | | |
|---|---|---|---|
| 4,444,186 | 4/1984 | Wolvek et al. | 606/194 |
| 4,571,240 | 2/1986 | Samson et al. | 604/96 |
| 4,582,181 | 4/1986 | Samson | 606/194 |
| 4,597,755 | 7/1986 | Samson et al. | 604/96 |
| 4,638,805 | 1/1987 | Powell . | |
| 4,715,378 | 12/1987 | Pope, Jr. et al. | 606/194 |
| 4,811,737 | 3/1989 | Rydell . | |
| 4,821,722 | 4/1989 | Miller et al. . | |
| 4,938,220 | 7/1990 | Mueller, Jr. . | |
| 4,998,923 | 3/1991 | Samson et al. | 606/194 |
| 5,049,130 | 9/1991 | Powell | 604/96 |

*Primary Examiner*—John D. Yasko
*Assistant Examiner*—Adam J. Cermak
*Attorney, Agent, or Firm*—Leydig, Voit & Mayer

[57] ABSTRACT

A self-venting balloon dilatation catheter and method for producing the same having a catheter tubing including a first lumen and a second lumen. An expandable balloon is positioned at a distal end of the catheter tubing. The first lumen is for a guide wire and the second lumen is in communication with the interior of the balloon. The balloon is expanded by filling the balloon with pressurized fluid via the second lumen. An air vent within the catheter tubing purges air from the balloon when the balloon is filled with fluid. Air purged via the air vent first moves substantially transverse to a longitudinal axis of the catheter tubing and then along the longitudinal axis to an opening at a distal end of the catheter tubing. A cylindrically marker band is secured around the distal end of the catheter tuving, and another cylindrical marker band is secured around the catheter tubing inside the expandable balloon.

10 Claims, 2 Drawing Sheets

SELF-VENTING BALLOON DILITATION CATHETER

FIELD OF THE INVENTION

The present invention relates generally to balloon dilatation catheters and, more particularly, to catheters having self-venting balloons.

BACKGROUND OF THE INVENTION

In recent years transluminal angioplasty has become increasingly popular as an effective alternative to coronary bypass surgery. Transluminal angioplasty utilizes an elongated, flexible catheter having a balloon or expandable member at its distal end that is inserted at an appropriate location in the system of a patient. After the catheter is inserted into the vascular system, it is routed through the vascular system to the coronary artery that is partially occluded by a stenotic lesion. Once the catheter is in place and the balloon is properly positioned relative to the lesion, the balloon is inflated by filling the balloon with a fluid that is under relatively high pressure. As the balloon expands, its opens the occluded vessel, thus allowing blood to flow more freely.

When the balloon-tipped catheter is initially removed from its sterile package in preparation for transluminal angioplasty surgery, it is necessary to purge air from inside the catheter prior to inserting the catheter into the patient. All of the air must be removed from the balloon because air compresses under pressure and prevents the balloon from inflating properly. More importantly, when the balloon is inflated with a radiopaque marking liquid, the presence of air in the balloon may result in an error in the accurate positioning of the balloon relative to the lesion being treated. Furthermore, air pockets create artifacts in an image formed by an ultrasonic device, such as that illustrated in U.S. Pat. No. 4,917,097 to Proudian which may be positioned within the balloon.

Conventional methods for purging air from the balloon involve repeatedly filling and aspirating the catheter with a liquid, such as saline solution, so that the air in the catheter tends to be mixed and entrapped in the liquid and drawn out of the catheter with the liquid. The problems associated with this technique have lead to many attempts to design a balloon that is self-purging of air.

Self-purging balloon catheters typically include an air vent that is large enough in diameter to enable air to pass from the balloon, but small enough in diameter to inhibit the flow of liquid from the balloon. While this approach is effective, most configurations of it are relatively costly to produce and test.

For example, conventional self-venting balloon catheters typically incorporate the self-venting feature into the balloon, requiring the balloon to be attached to the catheter before the self-venting feature can be tested. Because the vent is in the balloon, the self-venting feature cannot be tested until after the catheter is fully assembled. Because of the small size of the vents, it is not uncommon for them to not fully form. Because the flaw in the vent is not discoverable until after the catheter is fully assembled, the entire catheter must be discarded. Because the balloon is a relatively expensive component of the balloon catheter, it would be preferable to test the vent before the balloon is mounted to the catheter. Unfortunately, in most configurations of a self-venting balloon, this is not possible.

Furthermore, conventional self-venting balloon catheter configurations, such as those illustrated in U.S. Pat. No. 4,938,220 to Mueller and U.S. Pat. No. 4,638,805 to Powell, inhibit the visibility of bands mounted on the catheters and used as radiopaque markers. The configurations of these patents require a specially machined, split tip marker to be used in order to avoid interfering with the operability of the vent.

OBJECTS AND SUMMARY OF THE INVENTION

In view of the foregoing, it is a primary object of the present invention to provide a low-cost, self-venting balloon dilatation catheter whose venting function can be tested prior to final assembly of the catheter.

Another object of the present invention is to provide a self-venting element of a balloon that is not susceptible to collapse and closure during final assembly of the catheter.

A further object of the present invention is to provide a self-venting element that enables a highly visible cylindrical marker band to be easily mounted to the catheter tubing and applied completely around it without interfering with the operability of the vent.

Other objects and advantages will become apparent upon consideration of the following detailed description when taken in conjunction with the drawings.

In general, the invention provides for a self-venting dilatation balloon catheter and a method for constructing the catheter. The catheter has a first elongated tubing with an inner lumen and a second elongated tubing with an outer lumen. An expandable balloon is affixed to a distal end of the second elongated tubing, and the balloon is expanded by fluid supplied from the outer lumen which is connected to the balloon. An air vent is disposed longitudinally and transversely with respect to a longitudinal axis of the catheter to provide a passageway for air to pass from inside the balloon to outside the balloon, and the air vent is too small in diameter to enable liquid to pass through the vent.

In an alternative embodiment, the first elongated tubing is configured as a lamination of a first and second tubular member. The air vent hole is formed between the first and second tubular members and includes a passageway communicating the outer surface of the second tubular member to the portion of the vent between the two tubular members.

In still another alternative embodiment, the catheter is comprised of two extruded tubings of different cross section. One of the tubings forms the main body of the catheter and is intended to incorporate a cross-section that lends itself to a small diameter which maintains good "push-ability." The second tubing is formed from the inner tubing of either of the foregoing embodiments and is intended to be a short length of tubing that is glued to the distal end of the first tubing in order to form the complete length of the catheter tubing. The two tubings are butted together so that at least the guidewire lumens of the tubings are aligned. The balloon of the catheter is mounted so that the junction between the two tubings is under the balloon, thereby permitting the fluid lumen of the first tubing to be totally unaligned with the second tubing so that fluid flows into the cavity of the balloon.

While the invention will be described in connection with preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENTS

Figure 1:
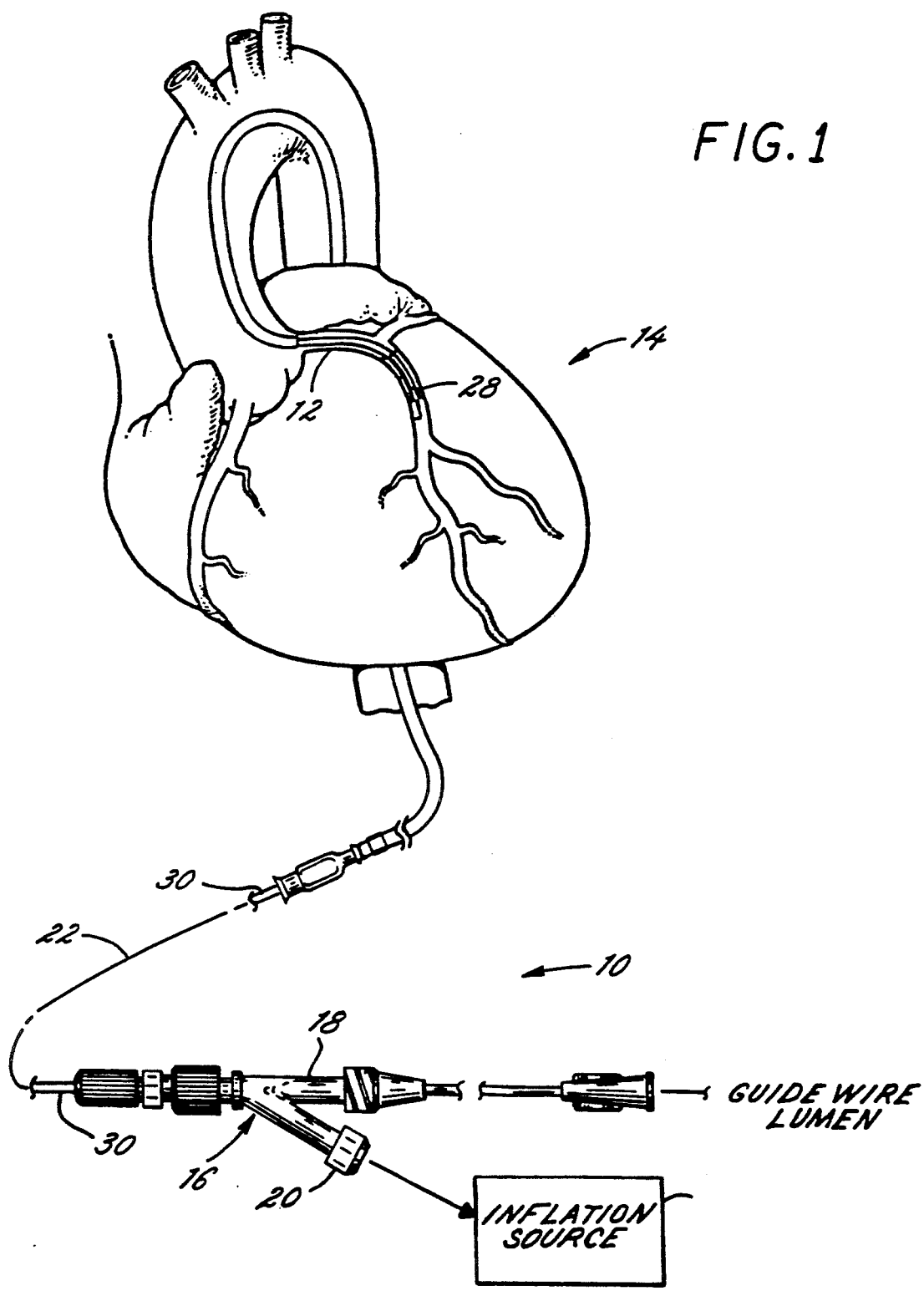
FIG. 1 is a schematic illustration of a balloon dilatation catheter according to the invention utilized for an angioplasty procedure in a coronary artery of a heart.
Figure 2A:
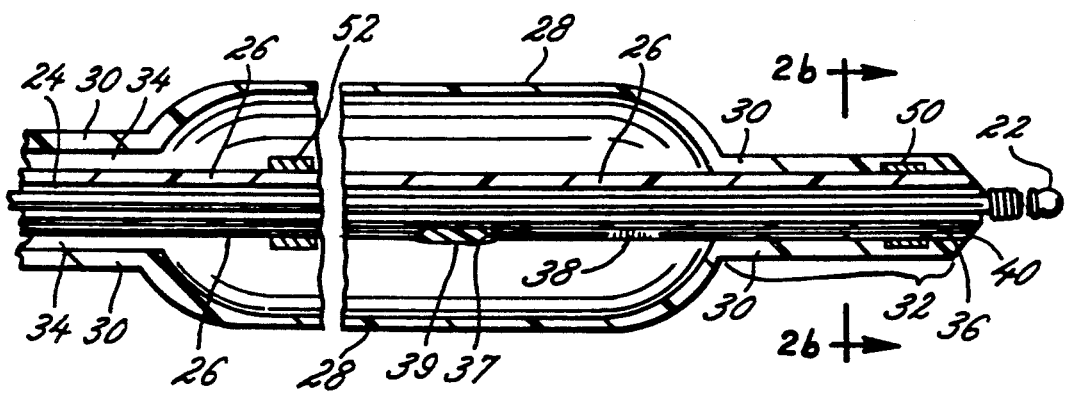
FIG. 2a is an enlarged cross-sectional view of a distal end of the balloon dilatation catheter shown in FIG. 1 taken along the longitudinal axis of the catheter.

Turning to the drawings, FIG. 1 illustrates a balloon dilatation catheter 10 according to the invention as it is being utilized in a coronary artery 12 of a heart 14. The catheter 10 includes a side arm adapter 16 which has a main or central arm 18 and a side arm 20. A guide wire 22 extends through the main or central arm 18 and through a first or inner lumen 24 of a flexible, first elongated tubing 26 (FIG. 2a). A distal end of the guide wire 22 is slightly rounded to facilitate insertion of the guide wire 22 into a vessel in a patient.

An inflating member or expandable balloon 28 is positioned near a distal end of a flexible, second elongated tubing or catheter tubing 30. The flexible tubing members 26 and 30 may be formed of a suitable flexible thermo-plastic material such as polyolefin or polyvinylchloride. The guide wire 22 extends through the first elongated tubing 26 and out its distal end 32.

The balloon 28 enwraps a portion of the first elongated tubing 26. The second elongated tubing 30 is coaxial to the first elongated tubing 26. Opposing ends of the balloon 28 are bonded in a suitable manner to the second elongated tubing 30 so as to form a liquid tight seal. Furthermore, the distal end 32 of the second elongated tubing 30 is also bonded to the first elongated tubing 26 so as to form a liquid-tight seal. The balloon 28 extends concentrically about the first elongated tubing 26. Although the balloon 28 can be formed as a separate element which has its extremities bonded to the second elongated tubing 30, the balloon 28 is preferably formed integral with the second elongated tubing 30 as shown.

An annular flow passage, second lumen, or outer lumen 34 is provided between the first elongated tubing 26 and the second elongated tubing 30. The outer lumen 34 opens into the balloon 28. The outer lumen 34 is in communication with the side arm 20 and receives the inflating fluid or liquid which can be introduced through the side arm 20 in a conventional manner to pass through the outer lumen 34 for inflating and deflating the balloon 28.

Although the preferred embodiment illustrates a balloon catheter having two continuous and concentric elongated tubings, wherein the inflating liquid flows in the lumen defined by the space between the two elongated tubings and the guidewire is received by the lumen formed by the interior bore of the inner elongated tubing, several other embodiments utilizing the present invention are possible. For example, the catheter may be formed of two separate lengths of tubing that are butted together. The longer or main length of tubing comprises virtually the entire length of the catheter, except for its distal end. This main tubing is formed by a conventional extrusion process to have two side-by-side lumens. The second length of tubing has the same structure as the inner tubing of either of the illustrated embodiments. The two tubings are butted together end to end and glued. In butting and gluing the two tubings, one of the two lumens in the main tubing is aligned with the lumen of the inner tubing in order to provide a continuous guidewire lumen through the catheter. The balloon is mounted over the junction of the two tubings such that the second lumen of the main tubing opens into the cavity of the balloon. This embodiment gives the catheter added strength enabling it to be pushed along the guidewire, while still enabling the catheter to be fairly flexible.

In accordance with one important aspect of the present invention, means are provided within the first elongated tubing for purging air from the balloon in response to the flow of pressurized fluid into the balloon by first forcing the air to move in a direction that is substantially transverse to a longitudinal axis of the catheter tubing and then along the longitudinal axis to an opening at the distal end of the catheter tubing. The longitudinal axis is defined by the guide wire 22 running through the inner lumen 24. A very small air vent hole 36 is disposed longitudinally or substantially aligned with respect to the axis of the catheter tubing 30 in the distal end 32 of the first elongated tubing 26, and the air vent hole 36 is disposed substantially transverse to the axis of the catheter tubing 30 within the first elongated tubing 26 to intersect the longitudinal portion of the air vent hole 36 at a point within the balloon 28.

The air vent hole 36 provides a passageway enabling air to escape from inside the balloon 28, but preventing inflating liquid or blood from passing through the air vent hole or passageway 36. The passageway 36 includes an internal aperture 38 located inside the balloon 28 at the transverse portion of the passageway 36. An external aperture 40 is located at an extreme distal point of the longitudinal portion of the passageway 36.

The passageway 36 of the air vent should be less than 0.001 inches in diameter. Air has a lower viscosity than the inflating fluid or blood. Thus, air can pass through the vent 36, but inflating fluid or blood cannot pass through it.

Figure 2B:
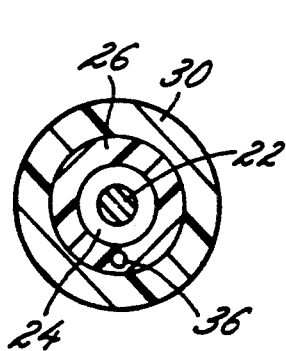
FIG. 2b is a cross-sectional view of the distal end of the catheter taken along the line 2b—2b of FIG. 2a, showing a transverse section of the catheter.

To make the catheter of FIGS. 2a-2b, the inner lumen 24 and the air vent 36 of the first elongated tubing 26 are formed over a die using a conventional extrusion process. The side-by-side lumen embodiment is produced by the same extruding process, except a different die is used.

As best seen in FIG. 2a, two apertures 37 and 38 are cut into an outer surface of the first or inner elongated tubing 26 in order to intersect the longitudinal portion of the air vent 36 formed in the extrusion process, but the apertures do not pierce the outer surface to a depth which would reach the inner lumen 24. The lumen forming the longitudinal portion of the air vent 36 is blocked by filling the proximal aperture 37 of the first elongated tubing 26 with a suitable material 39, thereby forming distal and proximal portions of the lumen which are not in communication with each other. The aperture 37 may be blocked with any suitable sealant such as an epoxy.

The gaseous continuity of the air vent 36 may now be tested before fitting the balloon 28 onto the first elongated tubing 26. This is a cost reduction feature of the present invention because it enables a defect in the air vent to be detected before completely assembling the balloon catheter. Other self-venting balloon catheters typically require the balloon to be fitted onto the catheter before the self-venting means may be tested. Furthermore, some conventional air vents are formed between the balloon and an inner tubular member and, therefore, are susceptible to collapse and closure. The present invention, however, eliminates these problems and the requirement of attaching the balloon to test the self-venting means, thus making more efficient use of time and materials.

Additionally, the material utilized to form the first or inner elongated tubing 26 is relatively inexpensive when compared to the cost of the material utilized to form the expandable balloon 28. Material utilized to form the balloon 28 is not wasted due to a defect in the self-venting means because a defect in the self-venting means will be detected before applying the balloon 28 to the catheter.

Figure 3A:
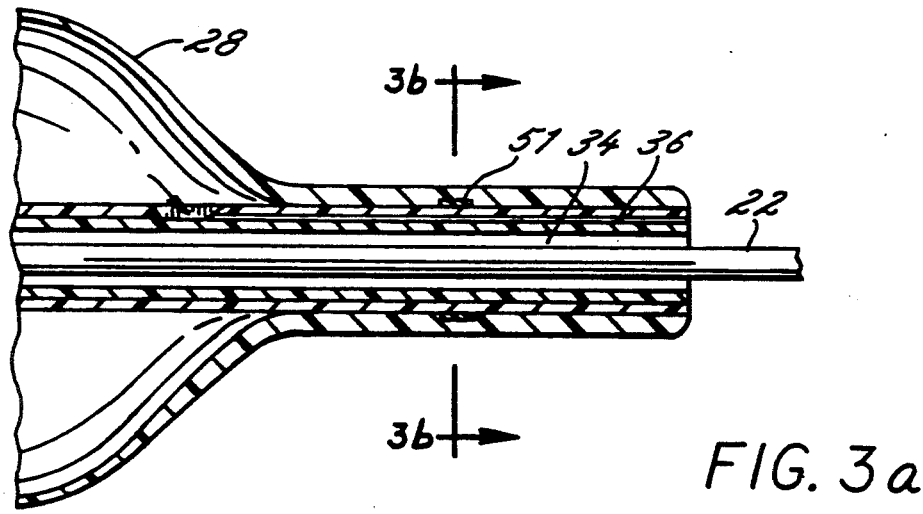
FIG. 3a is cross-sectional view of a second embodiment of the distal end of the catheter taken along the longitudinal axis of the catheter.
Figure 3B:
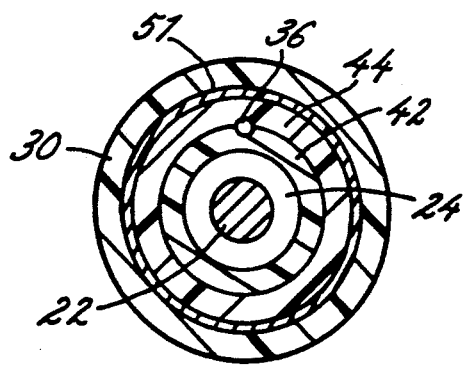
FIG. 3b is a cross-sectional view of the distal end of the catheter taken along line 3b—3b of FIG. 3a, showing a transverse section of the catheter.

In another embodiment of the present invention, the first or inner elongated tubing is formed from a lamination of a first tubular member 42 and a second tubular member 44 as illustrated in FIGS. 3a and 3b. The second tubular member 44 has a larger diameter than the first tubular member 42, and the second tubular member 44 is coaxial and contiguous to the first tubular member 42. In this embodiment, the longitudinal portion of the air vent 36 is disposed between the first and second tubular members 42, 44.

In the second embodiment, the air vent 36 is formed by placing a lubricated wire (not shown) between the first and second tubular members before they are bonded together in a suitable manner so as to form a liquid-tight seal between them. Typically, this can be accomplished by applying heat to the tubular members to shrink the tubular member 44 having a larger diameter onto the tubular member 42 having a smaller diameter, thereby forming the liquid-tight seal.

The wire placed between the first and second tubular members 42, 44 is removed after the tubular members 42, 44 have bonded together in order to leave an air vent hole 36 located between the first and second tubular members 42, 44. The wire should typically have a diameter of less than 0.001 inches and should be coated with a lubricant such as silicon or a lubricious material such as Teflon so that it may be easily removed to form the longitudinal portion of the air vent hole 36.

As with the first embodiment, the transverse portion of the air vent 36 is formed by cutting two apertures into the outer surface of the first elongated tubing 26, and then blocking the aperture furthest from the distal end of the air vent 36. Accordingly, the air vent 36 may be tested in the same manner as the first embodiment, thus providing savings of costs and time.

It is important to note that the air vent hole 36 does not necessarily need to be a hole, but instead may be filled with a material which is capable of passing air but inhibiting the passage of liquid.

In accordance with another object of the present invention, a fluoroscopically visible cylindrical band marker 50 is secured around the first elongated tubing 26 in order to permit the position of the distal end 32 of the catheter to be monitored as the catheter is inserted into the vascular system of the patient. Similarly, a second cylindrical band marker 52 is secured to the first elongated tubing 26 at a location within the balloon 28 in order to monitor the position of the balloon 28. The marker bands 50, 52 may be fabricated of gold, and have a wall thickness on the order to 0.003 inches and an internal diameter corresponding to the surface diameter of the first elongated tubing 26 by which the marker is to be mounted.

Conventional balloon catheters having self-venting elements prevent a cylindrical marker band from being secured to the distal end of an inner tubular member as the cylindrical band may interfere with the operability of the self-venting element. As a result, conventional designs, such as the one illustrated in U.S. Pat. No. 4,938,220 to Mueller, required a specially machined, split tip marker, which is crimped onto the inner tubular member, in order to prevent interfering with the operability of the self-venting element. The air vent is positioned between opposing ends of the semi-cylindrical band.

The present invention, however, enables fully-cylindrical marker bands to be employed directly over the first elongated tubing 26 without interfering with the air vent 36 as best seen in connection with the band 51 of FIGS. 3a-3b. Such a design is less costly to produce because the added step of cutting the cylindrical band into a semi-cylindrical band. Moreover, a completely cylindrical marker band is more visible in fluoroscopic monitoring procedures than a semi-cylindrical marker band.

In using the catheter of FIGS. 2a-2b, the distal end 32 of the first elongated tubing 26 is raised upward so that when the balloon 28 is filled with liquid, air bubbles within the balloon 28 will rise toward the air vent hole 36. The balloon 28 is first inflated outside the body of the patient by introducing a liquid through the side arm 20 so that the inflating liquid passes through the outer lumen 34 between the first and second elongated tubings 26, 30 and passes into the balloon 28. The air which is in the balloon 28 is pushed upward in the balloon 28 and, under the pressure of the liquid, the air is forced out through the air vent hole 36. As soon as the balloon 28 has been inflated with the inflating liquid and the air has been expelled from the balloon 28 by way of the vent 36, contracting characteristics of the balloon 28 and ambient pressure are allowed to substantially deflate the balloon 28.

Up to this time, no suction or source of negative pressure is applied to withdraw the liquid out of the balloon 28 via the outer lumen 34. The catheter having a substantially deflated balloon 28 is then inserted into the vascular system of the patient, but only so far as to insert the distal end 32 of the second elongated tubing 30. The remaining liquid is then withdrawn from the balloon 28 by applying a negative pressure at a posterior end of the outer lumen 34 in order to substantially remove all the liquid from the balloon 28. The viscosity of blood prevents any substantial amount of blood from the patient's vascular system from being drawn into the balloon 28 via the vent 36 during this latter deflation procedure. Once the negative pressure expels the liquid from the balloon 28 causing the balloon 28 to collapse and wrap itself closely around the first elongated tubing 26, the balloon 28 assumes its low profile state and is ready to be completely inserted into the vascular system of the patient of the angioplasty procedure.

We claim as our invention:

1. A dilatation catheter having distal and proximal ends, comprising in combination:
   an elongated tubing having at least one lumen and longitudinal and transverse axes;
   an expandable balloon at a distal end of the elongated tubing in communication with a pressurized fluid for expanding the balloon by way of the at least one lumen; and
   a passageway within the elongated tubing having a substantially uniform diameter for purging air from inside the balloon to an ambient environment of the balloon while at the same time preventing the pressurized fluid from passing through the passageway to the ambient environment, the passageway terminating at one end in a first aperture passing through an outer surface of the elongated tubing inside the balloon and terminating at a second end in a second aperture disposed at the distal end of the elongated tubing, wherein the first aperture faces along the transverse axis and the second aperture faces along the longitudinal axis so that the flow of pressurized fluid into the balloon forces the air to move through the first aperture substantially along the transverse axis and through the passageway along the longitudinal axis to the second aperture to purge air from the balloon.

2. The dilatation catheter as defined in claim 1, wherein the distal end of elongated tubing is comprised of a first and a second tubular member, the second tubular member encompassing the first tubular member and contiguous and coaxial to it.

3. The dilatation catheter as defined in claim 2, wherein the substantially aligned portion of the passageway is disposed between the first and second tubular members.

4. The dilatation catheter as defined in claim 1, further comprising:
   a cylindrical marker band having an inner diameter substantially equal to a surface diameter of the distal end of said elongated tubing, said cylindrical marker band being secured around the distal end of said elongated tubing.

5. The dilatation catheter as defined in claim 4, further comprising:
   a second cylindrical marker band having an inner diameter substantially equal to a surface diameter of said elongated tubing inside said expandable balloon, said second cylindrical marker band being secured around the portion of said elongated tubing that is located inside the expandable balloon.

6. A dilatation catheter having distal and proximal ends, comprising in combination:
   a catheter tubing having an expandable balloon surrounding a distal end of the catheter tubing and longitudinal and transverse axes;
   a first lumen within the catheter tubing sized to smoothly follow a guidewire disposed within the first lumen;
   a second lumen within the catheter tubing for communicating pressurized fluid to expand the balloon; and
   a passageway within the catheter tubing having a substantially uniform diameter for purging air from inside the balloon to an ambient environment of the balloon while at the same time preventing the pressurized fluid from passing through the passageway to the ambient environment, the passageway terminating at one end in a first aperture passing through an outer surface of the catheter tubing inside the balloon and terminating at a second end in a second aperture disposed at the distal end of the catheter tubing, wherein the first aperture faces along the transverse axis and the second aperture faces along the longitudinal axis so that the flow of pressurized fluid into the balloon forces the air to move through the first aperture substantially along the transverse axis and through the passageway along the longitudinal axis to the second aperture.

7. The dilatation catheter as defined in claim 6, wherein the catheter tubing is composed of a first and a second tubular member, the second tubular member encompassing a first tubular member and being contiguous and coaxial to the first tubular member.

8. The dilatation catheter as defined in claim 7, wherein the substantially aligned portion of the passageway is disposed between the first and second tubular members.

9. The dilatation catheter as defined in claim 6, further comprising:
   a cylindrical marker band having an inner diameter substantially equal to a surface diameter of the distal end of said catheter tubing, said cylindrical marker band being secured around the distal end of said catheter tubing.

10. The dilatation catheter as defined in claim 9, further comprising:
    a second cylindrical marker band having an inner diameter substantially equal to a surface diameter of said catheter tubing inside the expandable balloon, said second cylindrical marker band being secured around the portion of the catheter tubing that is located inside the expandable balloon.

* * * * *

UNITED STATES PATENT AND TRADEMARK OFFICE
CERTIFICATE OF CORRECTION

PATENT NO. : 5,135,486
DATED : August 4, 1992
INVENTOR(S) : MICHAEL J. EBERLE AND TIM CORTEZ It is certified that error appears in the above-identified patent and that said Letters Patent is hereby corrected as shown below:

ON THE TITLE PAGE:

[54] TITLE

Delete "DILITATION" and substitute therefor -- DILATATION --.

[57] ABSTRACT

Line 14, delete "cylindrically" and substitute therefor -- cylindrical --; and

Line 15, delete "tuving" and substitute therefor -- tubing --.

Column 1, line 1, delete "DILITATION" should read --DILATATION--.
Column 8, line 32, delete "composed" and substitute --comprised--.

Signed and Sealed this

Fourteenth Day of September, 1993

Attest:

BRUCE LEHMAN

Attesting Officer

Commissioner of Patents and Trademarks